US011078432B2

(12) United States Patent
Yang et al.

(10) Patent No.: US 11,078,432 B2
(45) Date of Patent: Aug. 3, 2021

(54) HYDRODEOXYGENATION OF LIGNIN TO HYDROCARBONS USING BIMETALLIC CATALYSTS

(71) Applicant: WASHINGTON STATE UNIVERSITY, Pullman, WA (US)

(72) Inventors: Bin Yang, Pullman, WA (US); Hongliang Wang, Pullman, WA (US)

(73) Assignee: WASHINGTON STATE UNIVERSITY, Pullman, WA (US)

( * ) Notice: Subject to any disclaimer, the term of this patent is extended or adjusted under 35 U.S.C. 154(b) by 0 days.

(21) Appl. No.: 16/990,077

(22) Filed: Aug. 11, 2020

(65) Prior Publication Data

US 2020/0377803 A1 Dec. 3, 2020

Related U.S. Application Data

(62) Division of application No. 16/340,964, filed as application No. PCT/US2017/057092 on Oct. 18, 2017, now abandoned.

(60) Provisional application No. 62/410,203, filed on Oct. 19, 2016.

(51) Int. Cl.
| | | |
|---|---|---|
| C07C 13/18 | (2006.01) | |
| C10G 45/12 | (2006.01) | |
| C07C 1/22 | (2006.01) | |
| B01J 29/14 | (2006.01) | |
| C10G 3/00 | (2006.01) | |
| B01J 35/10 | (2006.01) | |
| B01J 29/12 | (2006.01) | |
| B01J 29/08 | (2006.01) | |
| C07C 13/28 | (2006.01) | |
| C10L 1/10 | (2006.01) | |
| B01J 37/02 | (2006.01) | |
| C10G 45/06 | (2006.01) | |
| C10L 1/04 | (2006.01) | |
| C10L 1/16 | (2006.01) | |

(52) U.S. Cl.
CPC ............ *C10G 45/12* (2013.01); *B01J 29/088* (2013.01); *B01J 29/126* (2013.01); *B01J 29/146* (2013.01); *B01J 35/1023* (2013.01); *B01J 35/1038* (2013.01); *B01J 35/1061* (2013.01); *B01J 37/0201* (2013.01); *C07C 1/22* (2013.01); *C07C 13/18* (2013.01); *C07C 13/28* (2013.01); *C10G 3/44* (2013.01); *C10G 3/45* (2013.01); *C10G 3/49* (2013.01); *C10G 3/50* (2013.01); *C10G 45/06* (2013.01); *C10L 1/04* (2013.01); *C10L 1/10* (2013.01); *C10L 1/1691* (2013.01); *B01J 2229/186* (2013.01); *C07C 2523/06* (2013.01); *C07C 2523/46* (2013.01); *C07C 2523/72* (2013.01); *C07C 2523/745* (2013.01); *C07C 2523/755* (2013.01); *C07C 2523/78* (2013.01); *C07C 2523/89* (2013.01); *C07C 2529/12* (2013.01); *C07C 2529/14* (2013.01); *C07C 2601/14* (2017.05); *C10G 2300/1014* (2013.01); *C10G 2300/202* (2013.01); *C10L 2200/0469* (2013.01); *Y02P 30/20* (2015.11)

(58) Field of Classification Search
CPC .. C10L 1/04; C10L 1/10; C10L 1/1691; C10L 2220/0469; C10L 2220/0484; C10L 2200/0469; C10L 2200/0484; C10G 3/44; C10G 3/49; C10G 3/45; C10G 3/50; C10G 45/06; C10G 45/12; C10G 2300/202; C10G 2300/1014; C07C 1/22; C07C 13/18; C07C 13/28; C07C 2601/14; C07C 2529/14; C07C 2529/12; C07C 2523/06; C07C 2523/46; C07C 2523/745; C07C 2523/72; C07C 2523/78; C07C 2523/755; C07C 2523/89; Y02P 30/20
USPC .......... 585/240, 242, 469; 44/307, 605, 628; 208/67, 68, 111.3, 111.35, 112, 113, 118, 208/119, 120.15, 120.25, 120.35, 430, 208/431, 435, 438, 428
See application file for complete search history.

(56) References Cited

U.S. PATENT DOCUMENTS

| | | | | |
|---|---|---|---|---|
| 6,953,873 | B2 * | 10/2005 | Cortright | C10G 3/47 585/733 |
| 7,022,888 | B2 * | 4/2006 | Choudhary | C07C 1/20 585/639 |
| 2012/0323053 | A1 * | 12/2012 | Qiao | C10G 1/065 568/959 |
| 2013/0079566 | A1 * | 3/2013 | Lin | B01J 23/34 585/242 |
| 2013/0255138 | A1 * | 10/2013 | Mayeur | C10G 3/47 44/307 |
| 2014/0273118 | A1 * | 9/2014 | Held | C10G 3/47 435/136 |
| 2014/0335586 | A1 * | 11/2014 | Zhang | C10G 3/46 435/167 |

(Continued)

OTHER PUBLICATIONS

Laskar et al., "Noble-metal catalyzed hydrodeoxygenation of biomass-derived lignin to aromatic hydrocarbons", Green Chem., 2014, 6, pp. 897-910.*

(Continued)

*Primary Examiner* — Elizabeth D Wood
(74) *Attorney, Agent, or Firm* — W&C IP

(57) ABSTRACT

Bimetallic catalysts for the hydrodeoxygenation (HDO) conversion of lignin into useful hydrocarbons are provided. The catalysts are bifunctional bimetallic ruthenium catalysts Ru-M/X$^+$Y comprising a metal M such as iron (Fe), nickel (Ni), copper (Cu) or zinc (Zn), zeolite Y and cation X$^+$ (e.g. H$^+$) associated with zeolite Y.

8 Claims, 11 Drawing Sheets

(56) References Cited

U.S. PATENT DOCUMENTS

2015/0099868 A1* 4/2015 Yang ................. B01J 19/24
530/503
2015/0183701 A1* 7/2015 Blank ................ C07D 307/08
568/652

OTHER PUBLICATIONS

Zhang et al., "Hydrodeoxygenation of Lignin-Derived Phenolic Monomers and Dimers to Alkane Fuels over Bifunctional Zeolite-Supported Metal Catalysts", ACS Sustainable Chem. Eng. 2014, 2, pp. 683-691.*
Pineda et al., "Heterogeneously catalyzed lignin depolymerization", Appl Petrochem Res, 2016, 6, pp. 243-256.*
Zhang and Teo et al., "A seriies of NiM (M=Ru, Rh and Pd) Bimetallic Catalysts for Effective Lignin Hydrogenolysis in Water", ACS Catal. 2014, 4, pp. 1574-1583.*

* cited by examiner

HYDRODEOXYGENATION OF LIGNIN TO HYDROCARBONS USING BIMETALLIC CATALYSTS

CROSS-REFERENCE TO RELATED APPLICATIONS

This application is divisional application of U.S. Ser. No. 16/340,964 filed Apr. 10, 2019, which itself was a national stage filing under Rule 371 of PCT/US2017/057092 filed Oct. 18, 2017, which claimed priority to USSN 62/410,203 filed Oct. 19, 2016.

This invention was made with government support under DTOS59-07-G-00055 awarded by the United States U.S. Department of Transportation and DE-AC36-08GO28308 awarded by the United States Department of Energy. The government has certain rights in the invention.

DESCRIPTION

Background of the Invention

Field of the Invention

The invention generally relates to bimetallic catalysts for the hydrodeoxygenation (HDO) conversion of lignin into useful hydrocarbons. In particular, the invention provides a bifunctional bimetallic ruthenium catalyst Ru-M/X$^+$Y comprising a metal M such as iron (Fe), nickel (Ni), copper (Cu) or zinc (Zn); zeolite Y (sometimes referred to as Y zeolite or H+—Y zeolite); and cation X$^+$ associated with zeolite Y.

Background of the Invention

Lignin is one of the major three components in lignocellulosic biomass, and it is also the only large-volume renewable resource that is mainly made up of aromatics. Lignin has higher C/O ratio and energy density than the other two biomass components namely cellulose and hemicellulose (carbohydrates). Compared with carbohydrates, lignin is quite heterogeneous, consisting of several kinds of phenylpropanoid units linked by various C—O—C and C—C bonds. Given its three-dimensional, highly branched chemical structure, lignin is rather stubborn to convert selectively under either thermal, catalytic, or biological conditions. These difficulties significantly hinder the use of lignin by biorefineries for commercial production of e.g. biofuels. As a matter of fact, most of the existing biorefinery processes, such as bioethanol production, currently focus on the utilization of cellulose or hemicellulose, which then result in tremendous amount of lignin as waste or as a low value-added solid fuel. Therefore, the efficient utilization of lignin for the production of value-added chemicals or advanced biofuels will undoubtedly contribute to the modern lignocellulosic biorefineries. Increasing attention has been received in recent years for lignin valorization, and also various processes have been attempted, but the selective conversion of lignin to the well-defined products is still a nascent endeavor.

Hydrodeoxygenation (HDO) refers to a hydrogenolysis process for removing oxygen from oxygen containing compounds conversion of lignin, in which lignin is depolymerized and deoxygenated by using hydrogen over catalysts, is regarded as one of the most promising ways to transform lignin into value-added aromatics or fuel-range hydrocarbons. However, to make this process industrially viable, several challenges, especially the development of highly effective catalysts with low cost, must be addressed.

Ru containing catalysts have been used to catalyze lignin HDO but suffer from excessive hydrogenolysis and the formation of undesirable low molecular gas products.

It would be of benefit to have available highly effective but low cost catalysts for the HDO conversion of lignin, that do not have the disadvantages of prior art catalysts.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

The synthesis of high-efficiency and low-cost catalysts for HDO of waste lignin into useful products (such as biofuel) is crucial for enhancing current biorefinery processes. According to the present invention, inexpensive transition metals, including Fe, Ni, Cu, or Zn, were co-loaded with Ru on H$^+$—Y zeolite to form bimetallic and bifunctional catalysts. The catalysts were tested for HDO conversion of softwood lignin and several lignin model compounds, and they exhibited highly efficient catalytic properties. The results also indicated that the new catalysts mitigated the hydrogenolysis activity of Ru and thus decreased the yield of undesirable low molecular gas products. Moreover, all the bifunctional catalysts proved to be superior to the combination catalysts of Ru/Al$_2$O$_3$ and H$^+$—Y zeolite, which have been described in the prior art (Wang, et al., Green Chemistry 2015, 17, 5131-5135; Hongliang et al., Green Chemistry, 2016, 18, 2802-2810.DOI: 10.1039/c5gc02967; Hongliang et al., ACS Sustainable Chemistry & Engineering, 2017, 1824-1830. DOI: 10.1021/acssuschemeng.6b02563, Publication Date (Web): 5 Jan. 2017).

It is an object of this invention to provide a bifunctional bimetallic catalyst having a chemical formula Ru-M/XY, where M is a metal, Y is a Y zeolite and X is a cation associated with the Y zeolite. In some aspects, M is selected from the group consisting of Fe, Ni, Cu, and Zn. In other aspects, the cation is selected from the group consisting of H+, Na$^+$, K$^+$ and NH$^{4+}$.

The invention also provides a method of producing at least one hydrocarbon from lignan, comprising i) exposing a reaction mixture comprising lignin to a bimetallic catalyst having of chemical formula Ru-M/XY, where M is a metal, Y is a Y zeolite and X is a cation associated with the Y zeolite, wherein the step of exposing is performed under conditions suitable for hydrodeoxygenation of lignin in the reaction mixture; and ii) recovering at least one hydrocarbon from the reaction mixture after hydrodeoxygenation of the lignin. In some aspects, M is selected from the group consisting of Fe, Ni, Cu, and Zn. In other aspects, the cation is selected from the group consisting of H+, Na$^+$ K$^+$ and NH$^{4+}$. In further aspects, the at least one hydrocarbon is a cyclohexane derivative. In additional aspects, the cyclohexane derivative is selected from the group consisting of methylcyclohexane, ethylcyclohexane, 1,1'-bi(cyclohexane), dicyclohexylmethane and 1,2-dicyclohexylethane. In yet additional aspects, the at least one hydrocarbon is a fuel or a fuel additive. In some aspects, the fuel or the fuel additive is selected from the group consisting of a paraffin, an alkylbenzene, an indan, a tetralin, naphthalene, a substituted naphthalene, a cycloolefin, a cyclohexanone and a cyclohexanol derivative. In other aspects, the fuel or the fuel additive is a paraffin and the paraffin is a monocycloparaffin, a dicycloparaffin or a tricycloparaffin.

The invention also provides a method of making a bifunctional bimetallic catalyst, comprising loading ruthenium and a metal M onto a zeolite support Y comprising an associated cation X. In some aspects, the metal M is selected from the group consisting of Fe, Ni, Cu, and Zn. In other aspects, the cation X is selected from the group consisting of H+, Na$^+$, K$^+$ and NH$^{4+}$. In further aspects, the step of loading is performed by a technique selected from the group consisting of ion exchange with metal cations in liquid solution, impregnation with a metal salt solution, ion-adsorption, precipitation and a sol-gel technique.

DETAILED DESCRIPTION

Figure 1:
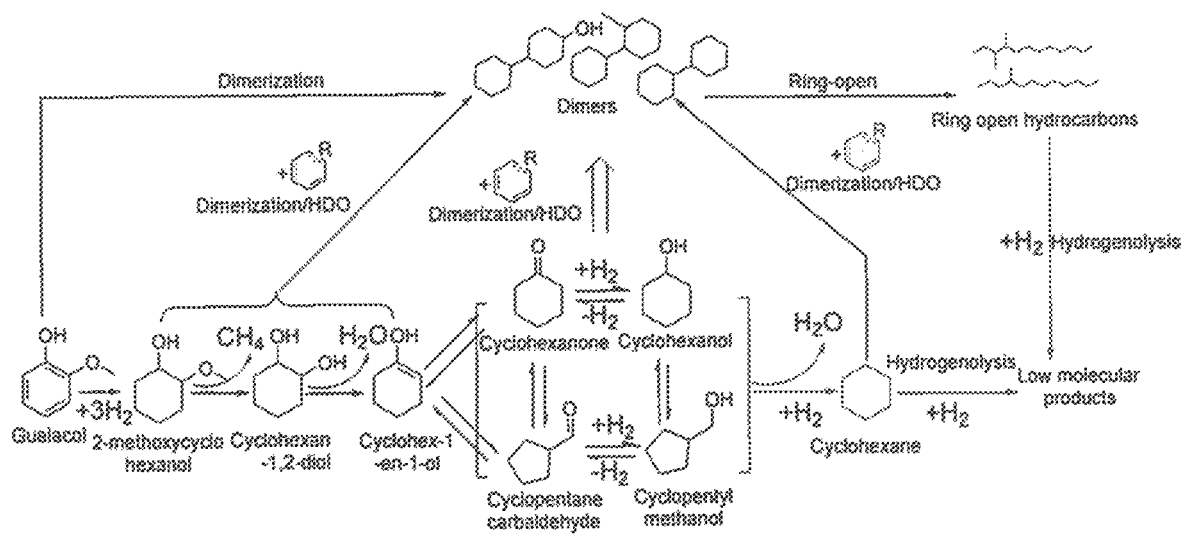
FIG. 1. Proposed reaction pathway of guaiacol with bifunctional catalysts.

The present disclosure provides bimetallic catalysts that efficiently catalyze the HDO conversion of lignin to useful platform products. By selecting suitable combinations of metals, it was possible to produce catalysts with significantly higher activity than prior art catalysts. Advantageously, the metals used in the catalysts are relatively inexpensive. Thus, earth abundant metals, including Fe, Ni, Cu, Zn, were used to partially replace the noble metal (Ru) to synthesize bimetallic catalysts supported on the exemplary zeolite H$^+$—Y. The H$^+$—Y zeolite was chosen as an exemplary zeolite because it possesses a high concentration of active acid sites. The resulting bimetallic catalysts exhibit remarkable hydrolysis and HDO activities toward lignin, and may be used in other reactions as well.

Without being bound by theory, it is believed that the success observed with the particular metal combinations disclosed herein can be explained as follows: The electronic environment of the metals in bimetallic catalysts is changed by the formation of heteroatom bonds, which can lead to modifications of the electronic structure of metals through the ligand effect. Also, the formation of heterogeneous metal-metal bonds in bimetallic catalysts can cause changes in orbital overlap, resulting in a strain effect that can alter the geometry of the bimetallic structures. Thus, both electronic structure and surface geometry have effects on catalytic performance and have been improved in the present catalysts, compared to the prior art.

Definitions

Hydrodeoxygenation (HDO) refers to a hydrogenolysis process for removing oxygen from oxygen containing compounds. HDO conversion of lignin causes deoxygenation and also depolymerization of lignan. The overall lignan HDO process proceeds by means of several kinds of reactions, including hydrogenolysis, hydrogenation, dehydration, dimerization and isomerization reactions of the products that are produced.

Y zeolites are derivatives of the faujasite mineral group which in turn is a member of the zeolite family. Zeolites are aluminosilicate compounds with an open network framework of corner-sharing [AlO$_4$]-groups, and [SiO$_4$]-groups, and Y zeolites in particular have a silica-to-alumina ratio in the framework of about 3 or higher (unlike X zeolites in which the ratio is between 2 and 3). Negative charges in the framework are balanced by the positive charges of associated cations in non-framework positions. Exemplary cations that may be associated with the framework include but are not limited to: H$^+$, Na$^+$, K$^+$, Mg$^{+2}$, Ca$^{+2}$, etc., and Y zeolites with any of these cations may be used in the practice of the invention.

Lignins are a class of complex organic structural polymers that make up the support tissues of vascular plants and some algae. Lignins are particularly important in the formation of cell walls, especially in wood and hark, because they lend rigidity and do not rot easily. Chemically, lignins are cross-linked phenolic polymers.

Catalyst Preparation

The catalysts described herein are prepared by any suitable method. Generally, the zeolite support (i.e., an H$^+$ Y zeolite) is obtained from a commercial source, many of which are known. The metals are incorporated or loaded into the zeolite framework using a suitable method, for example, by ion exchange with metal cations in a liquid solution, by impregnation with a solution of a metal salt, by ion-adsorption precipitation, by sol-gel technique, etc. In one aspect, the method used is an incipient wetness impregnation procedure with aqueous solutions of the metals salts as described in Zhang, et al. ACS Sustain Chem Eng, 2014, 2 (4), 683-691. Briefly, Zeolite Y is impregnated with an aqueous solution of metal salts. The resultant suspension is stirred for 24 h at room temperature followed by evaporation of the excess water at 55° C. The obtained solids are dried at 120° C. and calcined at 550° C. for 4 h with a ramp up of temperature of 10° C./min under air sparging. The catalysts are reduced at 250° C. for 2 h under 2. MPa H$_2$ before use.

In another aspect, monometallic catalysts of Ru/HY with a Ru loading of 5 wt % and bimetallic Ru-M/HY (M=Fe, Ni, Cu, Zn) catalysts with each metal loading of 2.5 wt % are prepared by using a conventional incipient wetness impregnation procedure with aqueous solutions of the metals salts. The resultant suspension is stirred for e.g. 24 h at room temperature followed by evaporation of the excess water at e.g. 55° C. The obtained solids are dried at e.g. 120° C. and calcined at e.g. 550° C. for 4 h with a ramp up of temperature of 10° C./min under air sparging. The catalysts are reduced e.g. at 250° C. for 2 h under 2 MPa $H_2$ before use. Wang, et al. *ChemSusChem*, 10, 1846-1856, 2017 describes a prior art incipient wetness impregnation procedure).

The reaction to prepare the catalyst typically is conducted at ambient temperature for a period of time ranging from about 2 to about 24 hours, e.g. for about 2, 4, 6, 8, 10, 12, 1.4, 16, 18, 20, 22 or 24 hours, depending on reaction conditions and the level of loading that is desired. Typically, a reaction is carried out for about 24 hours, e.g. with stirring or agitation of the reactants.

In general, the catalysts are loaded so as to contain from about 1-10% total metals, e.g. about 1, 2, 3, 4, 5, 6, 7, 8, 9 or 10% (or more) total metals. For example, the catalysts may contain about 5% total metals. In some aspects, if two metals are loaded, each is loaded at the level of about 2.5%, e.g. about 0.5, 1.0, 1.5, 2.0, 2.5. 3.0, 3.5, 4.0, 4.5 or 5.0%. The level of loading of each of the metals may be the same or different, e.g. both may be loaded at about 2.5%, or one may be loaded at about 2% and the other at about 3%, etc.

The size of the metal particles when loaded on the zeolite ranges from about 2 to about 12 nm in diameter, e.g. about 2, 3, 4, 5, 6, 7, 8, 9, 10, 11 or 12 nm, with the order of size increasing as Cu<Ni<Fe<Zn. For example, Cu particles are about 3-5 nm, Ni particles are about 3-6 nm, Fe particles are about 6-8 nm, and Zn particles are about 8~10 nm in diameter.

The BET surface area of the catalysts generally ranges from about 550 to about 750 $m^2/g$, e.g. from about 550, 575, 600, 625, 650, 700, 725 or 750 $m^2/g$.

The pore volume of the catalysts generally ranges from about 0.3 to about 0.5 $cm^3/g$, e.g. about 0.3, 0.31, 0.32, 0.33, 0.34, 0.35, 0.36, 0.37, 0.38, 0.39, 0.4, 0.41, 0.41, 0.43, 0.44, 0.45, 0.46, 0.47, 0.48, 0.49 or 0.5 $cm^3/g$.

The average pore diameter generally ranges from about 2 to about 3 nm, e.g. from about 2.0, 2.1, 2.2, 2.3, 2.4, 2.5, 2.6, 2.7, 2.8, 2.9 or 3.0 nm.

The number of acid sites on the catalysts ranged from about 2.5 to 6.0 mmol per g of catalyst, e.g. about 2.5, 3.0, 4.0, 4.5, 5.0, 5.5 or 6.0 mmol acid sites per g of (dried) catalyst.

After preparation, excess reactants and/or solvents are removed, e.g. by rinsing, evaporation, drying, calcination, etc., and the catalysts are stored until use. Prior to use, the catalysts are reduced (e.g. under pressurized $H_2$) and reduction generally occurs at an elevated temperature (e.g. 150 to 300° C.).

Methods of Using the Catalysts

The disclosure describes bimetallic catalysts and methods of their use to catalyze reactions of interest. In some aspects, the reaction of interest is the controlled hydrodeoxygenation (deconstruction, depolymerization, deoxygenation) of biomass such as lignin into fuels and platform chemicals, e.g. chemicals that can be used directly or that can be used in the synthesis of other useful products. However, the use of the catalysts in other reactions is not precluded is also encompassed), e.g. conversion of biomass platform chemicals (e.g. hydroxymethylfurfural and furfural) to fuels and chemicals, hydrodeoxygenation upgrading bio-oils, $CO_2$ reforming of methane, etc.

Lignan HDO methods generally comprise exposing a liquid lignocellulosic feedstock comprising lignin and a solvent (e.g. lignan in a reaction mixture) to at least one bimetallic catalyst as described herein. As used herein "lignan" refers to both purified lignan, partially purified/isolated lignan (e.g. from which cellulose and/or hemicellulose have been removed or largely removed, e.g. at least about 50, 60, 70, 80 or 90% or more removed), or a source that comprises lignan e.g. plant material, wood and pulp, paper, etc. any or all of which may be waste material. The lignan may be in any suitable physical form when it undergoes HDO, e.g. the lignan may be mechanically pretreated prior to exposure to the catalyst by chopping, milling, grinding, pulverizing, rolling into sheets, cutting, etc. so that it is provided in the form of chips, particles, slivers or threads, sheets, a powder, etc. The lignan may also be pretreated or treated chemically e.g. by kraft procedures, sulfite treatment, organosolvolysis, pyrolysis, steam, explosion, Ammonia Fibre Expansion (AFEX), hot water, dilute acid, etc., as is known in the art (e.g. see US patent application publications 20170145456, 20170253899, 20160215314 and 20140206046, the complete contents of each of which is herein incorporated by referenced in entirety). Generally, the pretreatment occurs before exposure to the catalyst; however, in some aspects, the two reactions are performed simultaneously, i.e. the lignan is exposed to the catalyst during a "pretreatment" procedure.

Prior to the HDO reaction, the lignan is generally mixed with a suitable liquid solvent to form a liquid feedstock. Suitable solvents include but are not limited to: aqueous water-based solvents which may e.g. alkaline water, various ionic liquids, alkanes, chloralkanes, polar aprotic solvents, deep eutectic solvents, etc. The HDO reaction typically takes place under conditions of high temperature and pressure. For example, the temperature is generally in the range of from about 100 to 350° C., e.g. about 100, 150, 200, 250, 300, 350, or greater, e.g. up to about 450° C. or higher).

The pressure for the reaction may be atmospheric pressure but is generally elevated e.g. in the range of from about 1-20 MPa (such as about 1, 2, 4, 6, 8, 10, 12, 14, 16 or 20 MPa).

The HDO reaction is generally carried out e.g. under an reduction gas such as $H_2$, or using hydrogen donating solvents such as isopropanol.

The amount of time for the HDO reaction varies depending e.g. on the lignan source and preparation, the pressure and temperature of the reaction, the solvents and other active agents that are used, etc. However, in general a HDO reaction is carried out for at least about 0.5-10 hours, e.g. for about 0.5, 1, 2, 3, 4, 5, 6, 7, 8, 9, or 10 hours or longer, e.g. for 12 hours or up to about 24 hours or more. If lower temperatures and/or pressures are used, the reaction may be carried out for a longer period of time.

The catalysts described herein may be used with (in association or conjunction with, before, after, at the same time, etc.) other methods that e.g. break the C—C bonds of lignan, including but not limited to, for example, cracking, hydrolysis, reduction, other catalysts, enzymatic hydrolysis, fermentation, etc. Similarly, various systems for producing bioproducts from biomass such as lignan are known and the catalysts described herein may be integrated into any suitable system, for example, those disclosed in US patent application publications 20170233327, 20160222475 and 20150353971, the complete contents of each of which is incorporated herein by referenced in entirety.

Products

Once an HDO recitation is complete, products are separated/recovered from the reaction mixture using any of several suitable means. For example, the liquor may be drained from the reaction mixture and the desired products contained therein may be retrieved by extraction with a suitable solvent (e.g. ethyl acetate), chromatography, centrifugation, filtering, precipitation, etc.

Useful products that are obtained from HDO reactions which employ the catalysts described herein include but are not limited to: hydrocarbons (e.g. saturated aromatics) with a carbon content of from about 8 to about 20 carbon atoms, including cyclohexane derivatives such as methylcyclohexane, ethylcyclohexane, 1,1'-bi(cyclohexane), dicyclohexylmethane, 1,2-dicyclohexylethane; hydrocarbons useful for fuels or as fuel additives such as Paraffins, Monocycloparaffins, Dicycloparaffins, Tricycloparaffins, Alkylbenzenes, Indans&tetralins, Naphthalene, Substituted naphthalenes, Cycloolefines, Cyclohexanone & Cyclohexanol derivatives; etc. exemplary uses of which are illustrated in the Table 1 below. The hydrocarbon yield is typically in the range of from at least about 25 to 30% or more (e.g. about 25, 26, 27, 28, 29, or 30% or more), and the typical level of lignin conversion is from at least about 70% to about 85%, such as about 70, 75, 80 or 85%. In some aspects, the hydrocarbon products are fuels or fuel additives, e.g. for jet fuels, (such as JP-8C, LP-8, JetA-1, QCF389 Diesel, Lignin Jet Fuel, LP-900RCO and JP-900 LCO, etc.) or other types of fuel (e.g. for automobiles, agricultural machinery, small engines, rockets, etc.).

content 48.02 wt %), anhydrous cuprous (II) chloride ($CuCl_2$, Cu content 47.28 wt %), nickel (II) chloride hydrate ($NiCl_2 \cdot 6H_2O$, 98% purity, Ni content 24.71 wt %) and ferric (III) chloride hydrate ($FeCl_3 \cdot 6H_2O$, 98% purity, Fe content 20.67 wt %) were purchased from Fisher scientific. Guaiacol, diphenyl ether, benzofuran and (benzyloxy)benzene were purchased from Sigma-Aldrich. Lignin was isolated from Lodgepole Pine sawdust.

Lignin Isolation and Purification

Softwood samples containing 0.5 g dry weight mass were loaded into a tubular reactor with a 20.5 ml working volume, which was then connected to an advanced sand fluid system. 0.05% (w/w) sulfuric acid at room temperature was pumped through the reactor to purge air and then used to pressurize the reactor to a set pressure of 300 psi-700 psi. The loaded biomass was completely wetted by this procedure. The reactors were heated to 250° C. in a 4-kW fluidized sand bath (model SBL-2D, Omega engineering, Inc., CT). The temperatures of the sand bath were set 15° C. higher than the target temperatures. The flow rate was set at 25 ml/min. After 8 min pretreatment, the reactor was cooled immediately with cold water. The liquid collected through the pretreatment was centrifuged at 1000 rpm, and the precipitate was washed with DI water and then was centrifuged again at 1000 rpm. Finally the precipitate lignin sample was frozen-dried and stored at room temperature for further use.

TABLE 1

Composition of jet fuels

| | World survey average[a] | Fischer-Tropsch JET A-l (s-8)[a] | Composite Jet A blend[a] | Coal-based jet fuel[a] | Lignin Jet Fuel[b] |
|---|---|---|---|---|---|
| Paraffins (n- + i-) | 58.8 | 99.7 | 55.2 | 0.6 | 6.2 |
| Monocycloparaffins | 10.9 | <0.2 | 17.2 | 46.4 | 3.9 |
| Dicycloparaffins | 9.25 | 0.3 | 7.8 | 47 | 60.9 |
| Tricycloparaffins | 1.08 | <0.2 | 0.6 | 4.6 | 1.9 |
| Alkylbenzenes | 13.4 | <0.2 | 12.7 | 0.3 | 0 |
| Indans&tetralins | 4.9 | <0.2 | 4.9 | 1.1 | <0.1 |
| Naphthalene | 0.13 | <0.2 | <0.2 | <0.2 | <0.1 |
| Substituted naphthalenes | 1.55 | <0.2 | 1.3 | <0.2 | <0.7 |
| Cycloolefines | — | — | — | — | 11 |
| Cyclohexanone & Cyclohexanol derivatives | — | — | — | — | 10.4 |

[a] Development of an Experimental Database and Kinetic Models for Surrogate Jet Fuels (see the website located at stanford.edu/group/pitsch/publication/ColketJet_Fuel_Surrogate_AIAA_2007.pdf)
[b] This application.

EXAMPLE

Hydrodeoxygenation of Lignin to Hydrocarbons By Using Inexpensive Bimetallic Catalysts Supported on Zeolite Y This example described the preparation, characterization and testing of bimetallic, bifunctional zeolite catalysts, and their use for the IMO of lignin into useful products. The catalysts were prepared using ruthenium (Ru) and relatively inexpensive transition metals, including Fe, Ni, Cu and Zn. The results showed that the catalysts displayed excellent catalytic properties. Significantly, the catalyst lessened the hydrogenolysis activity of Ru, thereby decreasing the amount of unwanted low molecular gas products generated during HDO.

Materials

Ruthenium (III) chloride hydrate ($RuCl_3 \cdot xH_2O$, Ru content 37 wt %), anhydrous zinc (II) chloride ($ZnCl_2$, Zn Catalyst Preparation Monometallic catalyst of $Ru/H^{30}$—Y with Ru loading of 5 wt. % and bimetallic $Ru-M/H^+$—Y (M=Fe, Ni, Cu, Zn) catalysts with each metal loading of 2.5 wt. % were prepared by using an incipient wetness impregnation procedure with aqueous solutions of the metals salts (Zhang, et al. ACS Sustain Chem Eng, 2014, 2 (4), 683-691). The resultant suspension was stirred for 24 h at ambient temperature followed by evaporating excess water at 55° C. The obtained solids were dried at 120° C. and calcined at 550° C. for 4 h with a ramp of 10° C./min under the air. The catalysts were reduced at 250° C. for 2 h under 2 MPa $H_2$ before use.

Catalyst Characterization

The catalytic materials synthesized in this work were characterized by X-ray diffraction (XRD), scanning transmission electron microscopy (STEM), $N_2$ physisorption Brunauer-Emmett-Teller (BET), and $NH_3$ temperature programmed desorption (TPD).

XRD patterns (FIGS. 7A-D, FIG. 8 and FIG. 9A-D) were taken with a Bruker D8 Venture diffractometer equipped with Cu tube operated at 40 W (40 kV, 1 mA). High angle annular dark-field (HAADF) scanning STEM images were taken on a probe-corrected FEI Titan™ 80-300 S/TEM operating at 300 kV.

$N_2$ physisorption analysis for determination of surface area and mesopore size was carried out using a Micromeritics ASAP™ 2020 volumetric analyzer at the liquid nitrogen temperature (77 K). The surface area was calculated by Brunauer-Emmett-Teller (BET) equation from the adsorption data obtained at $P/P_0$ values between 0.05 and 0.2. The average mesopore size was determined from the adsorption branch of the isotherm using the Barrett-Joyner-Halenda (BJH) algorithm. $NH_3$ temperature-programmed desorption ($NH_3$-TPD) measurements were performed in a quartz tube reactor equipped with a thermal conductivity detector (TCD). The samples (~50 mg) were degassed in a cell under pure He flow gas (50 mL/min) at 700° C. for 2 h (ramping rate=10° C./min) to remove the possible Si—OH groups that can potentially be dehydrated by making water. Then, the samples were treated with $O_2$ flow (10 mL/min) for 1 h, purged with pure He for 15 min, and treated with $H_2$ flow (10 ml/min) for 1 h. The samples were cooled down to ambient temperature in the cell under pure He flow and exposed to $NH_3$ gas for 20 min. After adsorption of $NH_3$ gas, the samples were purged with pure He flow for 30 min, and subsequently the cell was heated to 700° C. for $NH_3$ TPD measurement. The desorbed $NH_3$ molecules were monitored by thermal conductivity detector (TCD) upon increase of temperature.

Catalytic Hydrodeoxygenation (HDO) Reactions

In a typical reaction, lignin or lignin model compound (100 mg), water (30 ml) and catalyst (100 mg) were added to a Parr reactor (reactor volume=100 ml). The reactor was sealed and purged with $H_2$ for three times, and then pressurized with 4 MPa $H_2$ (room temperature). The reactions were carried out at 250° C. for 2 or 4 h. After each reaction, the reactor was cooled to room temperature to quench the reaction by immersing in a cold water bath. n-decane (5 μl) were added into the reaction solution used as internal standards for hydrocarbons calibrations. Ethyl acetate (30 ml) was used to extract the products from the reaction solution. After centrifugation at a speed of 10000 r/min for 10 min., the extract was separated and analyzed by GC-MS. The aqueous phase was filtered to recover solids which were made up of unreacted lignin, catalyst, and a small amount of char. The solids were washed 3× with each of DI water and ethanol. After that, the solids were dried at 105° C. for about 24 h, and then weighed.

Lignin Degradation Products Analysis

The organic solvent extracted samples (1 μl) were injected with 0.6 ml min$^{-1}$ of He (carrier gas) into a DB-5 (30 in length×250 μm I.D.×0.25 μm film thickness, J&W Scientific) capillary column fitted in an Agilent Technologies 7890A GC system set in the split less mode. The GC oven was programmed to 45° C. for 2 min; then it was raised at the rate of 15° C. per min until the temperature reached 200° C. and was held at this temperature for 1 min after which the temperature was raised at the rate of 5° C. until the temperature finally reached 280° C. and held at the final temperature for 7 min. Eluting compounds were detected with a MS (Agilent Technologies 5975C) inert XL EI/CI MSD with a triple axis detector, and compared using NIST libraries. A Shimadzu TOC-V Analyzer was used to quantify the total organic carbon of the lignin and residue solids (including catalyst and residue lignin). The effective carbon number (ECN) approach can be used for calculating relative response factors in cases where pure materials are not available for detector calibration (Scanion and Willis, Journal of Chromatographic Science, 1985, 23 (8), 333-340). Lignin conversion, the mass yield of each product and its selectivity were calculated as follows:

For the conversion of lignin model compounds:

$$Conversion = \frac{\text{Weight of initial model compounds} - \text{weight of remaining model compounds}}{\text{Weight of initial model compounds}} \times 100\%$$

$$Selectivity_x = \frac{\text{Weight of product } x}{\text{Weight of model compounds converted}} \times 100\%$$

For the conversion of lignin:

$$Conversion = \frac{\text{Carbon content original lignin} - \text{carbon content in residue solid}}{\text{Carbon content in original lignin}} \times 100\%$$

$$Yieldx(wt. \%) = \frac{\frac{\text{Mass n\_decane}}{142} \times \frac{areax/ECNx}{\text{area n\_decane}/10} \times MWx}{\text{Mass lignin}}$$

$$\text{Total product yield} = \sum_{x=1}^{25} Yieldx$$

Results and Discussion

Hydrodeoxygenation of Guaiacol Over Ru Based Bifunctional Catalysts Supported on H$^+$—Y zeolite Bifunctional catalysts with bimetals Ru-M/H$^+$—Y (M=Fe, Ni, Cu, Zn) were prepared and tested for lignin model compounds and softwood lignin HDO conversion in this study. Both Ru and inexpensive metal M loading were 2.5 wt % in all of the investigated bimetallic catalyst, while the Ru loading was 5 wt % when it was loaded alone.

Initially, the prepared catalysts were tested in the HDO of guaiacol, a typical lignin model compound, at 250° C. with 4 MP $H_2$ for 2 h. in an aqueous phase. Guaiacol was used as a model compound since it has three characteristic C—O bonds that are commonly encountered in lignin, namely $C_{methyl}$—OAr, $C_{aryl}$—OMe and $C_{aryl}$—OH, with the respective bond dissociation enthalpy (BDE) of 262-276, 409-421, and 466 kJ mol$^{-1}$.

TABLE 2

Hydrodeoxygenation of guaiacol over Ru/H⁺—Y and Ru—M/H⁺—Y (M = Fe, Ni, Cu, Zn) catalysts.[a]

Guaiacol → p1 Cyclohexanone + p2 Cyclohexanol + p3 Cclopentane carbaldehyde + p4 Cyclopentyl methanol + p5 Cyclohexane + p6 Dimers + p7 Ring-open Products + p8 etc. + $CH_4$, CO etc. Gases

| Catalyst | Conversion (wt. %) | Product selectivity (wt. %) | | | | | | | | Hydrocarbon Yield(p5~p7) |
|---|---|---|---|---|---|---|---|---|---|---|
| | | 1 | 2 | 3 | 4 | 5 | 6 | 7 | 8 | |
| Ru/H+—Y | 91 | 27.5 | 18.1 | 3.5 | 7.9 | 18.5 | 6.3 | 8.2 | 10.0 | 30.0 |
| Ru—Fe/H+—Y | 96 | 22.8 | 11.0 | 6.1 | 8.8 | 29.9 | 3.2 | 10.9 | 7.3 | 42.2 |
| Ru—Ni/H+—Y | 95 | 21.0 | 11.6 | 5.1 | 11.3 | 28.4 | 3.4 | 10.8 | 8.4 | 40.5 |
| Ru—Cu/H+—Y | >99 | 13.1 | 8.1 | 3.9 | 8.1 | 44.8 | 9.5 | 8.1 | 4.4 | 62.4 |
| Ru—Zn/H+—Y | >99 | 17.2 | 9.0 | 5.8 | 10.2 | 32.6 | 8.2 | 10.9 | 6.1 | 51.7 |

[a]Reaction conditions: water, 30 ml; catalyst, 100 mg; guaiacol, 100 mg; hydrogen pressure, 4 MPa; reaction temperature, 250° C.; reaction time 2 h.

Although guaiacol conversion was more than 90 wt. % over all of the investigated catalysts, it can be found in Table 1 that relatively higher lignin conversion had been obtained over bimetallic catalysts than over Ru/H⁺—Y. Especially, when Ru—Cu/H⁺—Y or Ru—Zn/H⁺—Y was used as catalyst, almost all of the guaiacol was converted. All the results indicate that the bimetallic catalysts possess higher HDO activities than that of Ru/Y. As can been seen in Table 1, mainly 8 kinds of products can be obtained after HDO of guaiacol over the investigated catalysts. Catechol, phenol, and benzene were usually observed as products or intermediates in guaiacol HDO reaction. However, none of these compounds were detected in our research, indicating the high hydrogenation activity of the prepared catalysts, which can achieve full aromatic ring saturation reaction. Products of p1~p4 contain oxygen functional groups, among which cyclohexanone (p1) and cyclohexanol (p2) are the common intermediates that can be typically found in guaiacol HDO reactions. While, interestingly, an obvious amount of p3 and p4, which were probably isomerized form p1 and p2, respectively, were unusually formed over all of the investigated catalysts, with slightly higher selectivities over bimetallic catalysts than that over Ru/H⁺—Y, indicating that the prepared bimetallic catalysts have relative high isomerization reactivity. Products of p5~p7 are hydrocarbons. Cyclohexane (p5) were derived from the complete HDO of guaiacol, while p6 and p7 were derived from dimerization and ring-open reactions during HDO, respectively. It can be found in Table 1 that all the investigated bimetallic catalysts can generate higher yield of cyclohexane than the monometallic catalyst. The highest yield of cyclohexane (about 45%) was obtained when Ru—Cu/H⁺—Y was used as HDO catalyst. Meanwhile, the total yield of the hydrocarbon products was close to 62% over Ru—Cu/H⁺—Y, indicating the superior HDO catalytic activity of this bimetallic catalyst.

Different properties of bimetallic catalysts from those of the corresponding monometallic catalysts, including the enhancement of hydrogenation activities, have been observed by previous researchers. According to their opinions, the enhancement of hydrogenation activities on the bimetallic surfaces has been correlated to the modification of the electronic properties due to the formation of the subsurface bimetallic structures.[18] To facilitate the hydrogenation reaction, one hypothesis is that an effective catalyst should bond relatively weakly to the reactants to keep the carbon-carbon and carbon-hydrogen bonds intact. Hammer and Nørskov have shown that the binding strength of molecules on transition metals is dependent on the electronic structure of the surface, by using the surface d-band center with respect to the Fermi level to describe the surface electronic property. Chen et al. have summarized experimental and theoretical studies that identify a nearly linear relationship between the binding energies and the surface d-band center for many adsorbates on a wide range of bimetallic surfaces. In the hydrogenation reaction, the shifts in the surface d-band center on the bimetallic surfaces affect the binding energy of both atomic and molecular adsorbates on the catalysts. Some of the bimetallic surfaces formed from 3 d transition metals (including Fe, Ni, Cu, Zn) and noble metals (such as Ru, Pt, Pd) with shifts of the d-band center closer to the Fermi level have been demonstrated to be more weakly bonded to reactants than the parent metals. Thus, compared with Ru/H⁺—Y, the enhanced HDO activity of the prepared bimetallic catalysts in our reaction could be probably attributed to the formation of the bimetallic structures with modified electronic properties.

The HDO of lignin and lignin model compounds include various kinds of reactions, such as hydrogenation, hydrogenolysis, dehydration, dimerization and isomerization reactions. Among the transition metals, Ru has been shown to be the most active catalyst for hydrogenolysis; however, it has been well known to have high rates of C—C bond cleavage, which leads to excessive production of low molecular products (C1~C4 gaseous products, Table 1 P8). The selectivities of gas products were lower over investigated bimetallic catalysts, indicating 3$d$ transition metals (M) in catalysts of Ru-M/H$^+$—Y (M=Ni, Fe, Cu, Zn) could mitigate the hydrogenolysis activity of Ru and improved the HDO behavior, which then resulted in high selectivity to high carbon number hydrocarbon products (C>5). Moreover, what is noteworthy is that when Cu was used to combine with Ru, lowest yield of gas product was achieved. Meanwhile, high selectivities to p5 (cyclohexane) and p6 (dimers) were obtained, suggesting Cu in Ru—Cu/H$^+$—Y could efficiently mitigate the hydrogenolysis activity of Ru while maintain high hydrodeoxygenation activity.

As mentioned above, no aromatic products were detected in the reaction, indicating all the synthesized catalysts have high hydrogenation activity towards completely saturating aromatic rings. Based on the obtained products, we proposed a reaction pathway of guaiacol hydrodeoxygenation conversion over acidic zeolite H$^+$—Y supported Ru and bimetallic Ru-M catalysts, and this is depicted in FIG. 1.

It was reported that the aromatic ring of guaiacol could be fully hydrogenated over acid-catalyst supported precious metal catalysis when heated from room temperature to ~108° C.[22] Thus, the first step of guaiacol HDO reaction in our studies probably involved the addition of 3 moles of hydrogen to the aromatic ring to generate a product of 2-methoxycyclohexanol. After that, 2-methoxycyclohexanol could be converted to cyclohexan-1,2-diol via the hydrogenolysis of C$_{methyl}$—O bond. The produced cyclohexan-1,2-diol could then go further dehydration reaction to form cyclohex-1-en-1-ol which could easily isomerize to yield cyclohexanone. However, none of the formation of 2-methoxycyclohexanol, cyclohexan-1,2-diol and cyclohex-1-en-1-ol was noted in our reactions, probably due to the high reactivity of these intermediates over the investigated catalysts.

Cyclohexanone was an important intermediate in our reaction, the selectivity of which was higher than other oxygen-containing intermediates. Hydrogenation of the aromatic ring in guaiacol (with 2-methoxycyclohexanol product), followed by a demethyoxylation and/or dehydroxylation pathway (with cyclohexanone/cyclohexanol and cyclohexane products) have been proposed in the HDO of guaiacol on Rh-based catalysts.[23] The passway in regard to cyclohexanone formation in our study is in agreement with that proposal but different from some other researches which reported that cyclohexanone was mainly obtained directly from phenol during guaiacol HDO reaction when Cu, Fe or Pt—Fe based materials were used as catalyst.[17] Cyclohexanone was not stable in the reaction. By the catalysis of acidic H$^+$—Y zeolite or oxides, cyclohexanone could isomerize to form cyclopentanecarbaldehyde (p3), or hydrogenate to produce cyclohexanol (p2) over metal catalysis, Cyclohexanol could go further dehydration reaction over acidic HY zeolite or oxides to generate cyclohexene which could be facilely hydrogenated to the main product of cyclohexane on metal. It is worth noting that though an obvious amount of cyclopentanecarbaldehyde (p3) and cyclopentylmethanol (p4) were detected in the reaction, the HDO products from them, such as cyclopentane and its derivatives, were not found, possibly because of the instability of these products which were prone to go over-hydrogenolysis reaction to form low molecular products Some dimers and ring-open products were also detected in the products, indicating the dimerization and ring-open reactions occurred during HDO.

Hydrodeoxygenation of Other Lignin Model
Compounds Over Ru Based Bifunctional Catalysts
Supported on H$^+$—Y zeolite

TABLE 3

Hydrodeoxygenation of lignin model compounds over Ru—Cu/H+—Y catalyst.[a]

| Substrate | Conversion | Product selectivity | | | | |
|---|---|---|---|---|---|---|
| | | 1 | 2 | 3 | 4 | 5 |
| Diphenyl ether (DPE) | 83 | 81.6 | 8.5 | 5.1 | 3.9 | 0.8 |

TABLE 3-continued

Hydrodeoxygenation of lignin model compounds over Ru—Cu/H+—Y catalyst.[a]

| Substrate | Conversion | Product selectivity | | | | |
|---|---|---|---|---|---|---|
| | | 1 | 2 | 3 | 4 | 5 |
| 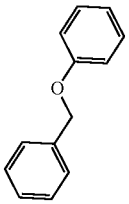<br>(Benzyloxy)benzene (BB) | >99 | <br>56.1 | 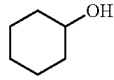<br>23.6 | 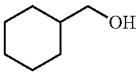<br>7.8 | 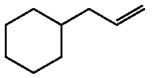<br>6.4 | 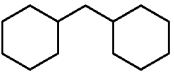<br>5.7 |
| 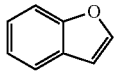<br>Benzofuran (BF) | >99 | 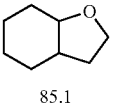<br>85.1 | 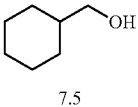<br>7.5 | 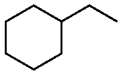<br>2.3 | 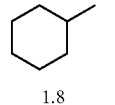<br>1.8 | 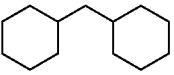<br>0.9 |

[a]Reaction conditions: water, 30 ml; catalyst, 100 mg; Lignin model compound, 100 mg; hydrogen pressure, 4 Mpa; reaction temperature, 250° C.; reaction time 2 h.

In order to further evaluate the HDO reactivity of the prepared bimetallic catalysts, Ru—Cu/H+—Y was selected as a representative catalyst for HDO of other several lignin model compounds, including diphenyl ether (DPE), (benzyloxy)benzene (BB) and benzofuran (BF).

DPE is a model compound of 4-O-5 linkage in lignin for investigating the aryl-O-aryl bond cleavage chemistry. The 4-O-5 bond is the strongest ether bond in lignin with a bond-dissociation energy (BDE) as high as 314 kJ mol$^{-1}$. The cleavage of an aryl-O-aryl bond usually requires harsh conditions. Without catalysts, the 4-O-5 bond was reported to be unreactive in water at temperatures below 500° C. In this study, DPE conversion was about 83% after reaction at 250° C. for 2 h, suggesting the high HDO reactivity of Ru—Cu/H+—Y. BB and BF represent the α-O-4 and β-5 structures in lignin, respectively. The HDO results indicated that both of these lignin model compounds could be totally converted. Cyclohexane was found to be the main product when DPE and BB were used as reactants. However, the prevailing HDO product from BF was found to be octahydrobenzofuran with the intramolecular ether bond remained intact. A small amount of (timer products (dicyclohexylmethane) was detected in the HDO products of BB and BF, suggesting that the dimerization reaction occurred after the breakage of the ether bond during the reaction.

Figure 2:
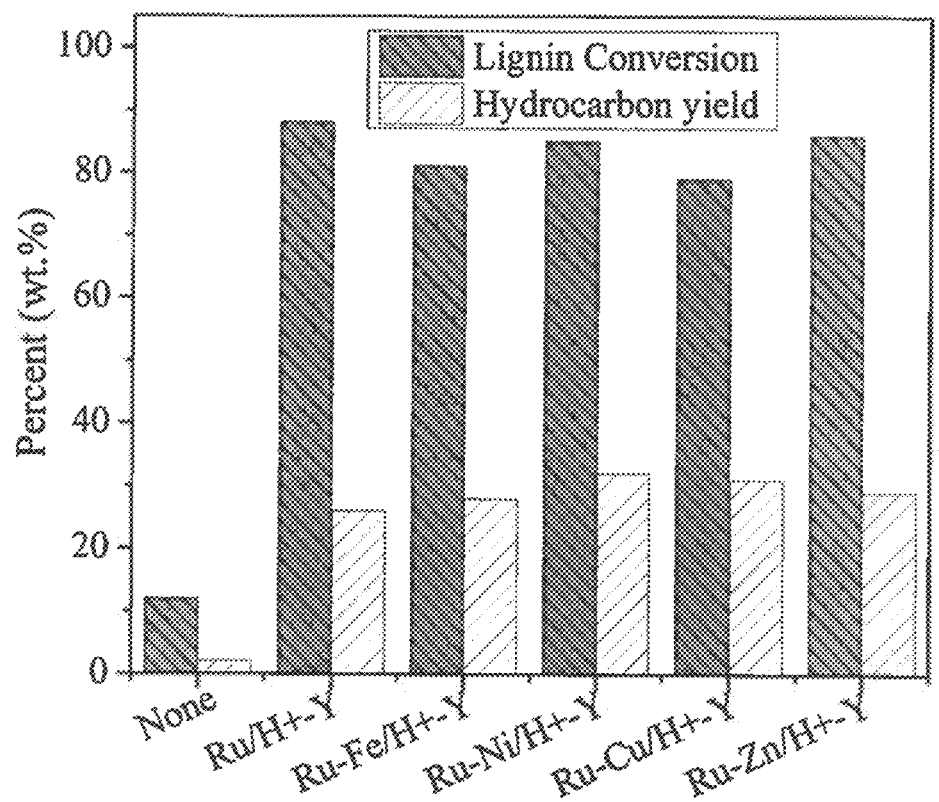
FIG. 2. Hydrodeoxygenation of soft wood lignin over various bimetal-HY catalysts. Reaction conditions: water, 30 ml; catalyst, 100 mg; lignin, 100 mg; hydrogen pressure, 4 Mpa; reaction temperature, 250° C.; reaction time 4 h.

Hydrodeoxygenation of Softwood Lignin Over Ru Based Bifunctional Catalysts Supported on H+—Y Zeolite The catalytic HDO activity of the prepared catalysts was further examined on softwood lignin. In a typical reaction, 100 mg pine wood lignin, 100 mg bifunctional catalyst were dispersed in 30 ml DI water and reacted at 250° C. under 4 MPa hydrogen for 4 h. After reaction, products were extracted by using 30 ml ethyl acetate and analyzed by GC-MS. The % conversion and hydrocarbon yields for the various catalysts are depicted in FIG. 2.

The conversion of lignin and the yield of detectable products were fairly low when there was no catalyst in the reaction. By adding the prepared catalysts, both lignin conversion and HDO product yield increased significantly, indicating the high HDO catalytic activity of these catalysts. Lignin conversion was found in the same level over all the five catalysts. Hydrocarbon selectivities were a little higher with Ru—Ni/H+—Y and Ru—Cu/H+—Y catalysis than that with others.

Figure 3:
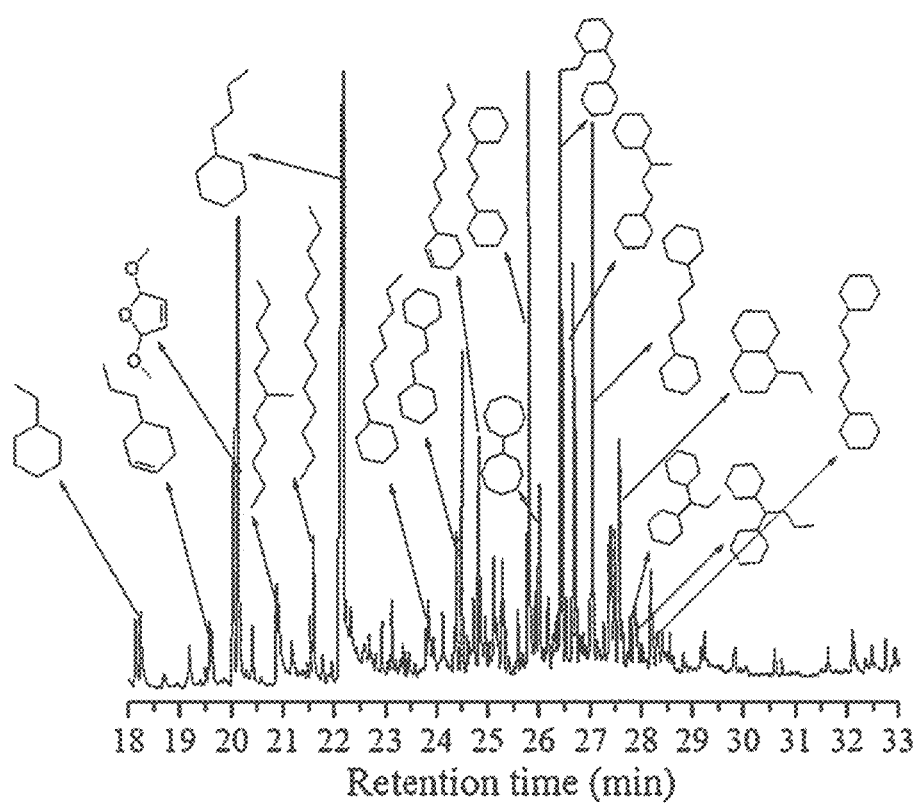
FIG. 3. GC-MS chromatogram of lignin conversion over Ru—Ni/H$^+$—Y and Ru—Cu/H$^+$—Y, catalysis. water, 30 ml; Ru—Cu/H$^+$—Y, 100 mg; lignin, 100 mg; hydrogen pressure, 4 MPa; reaction temperature, 250° C.; reaction time 4 h.
Figure 4A:
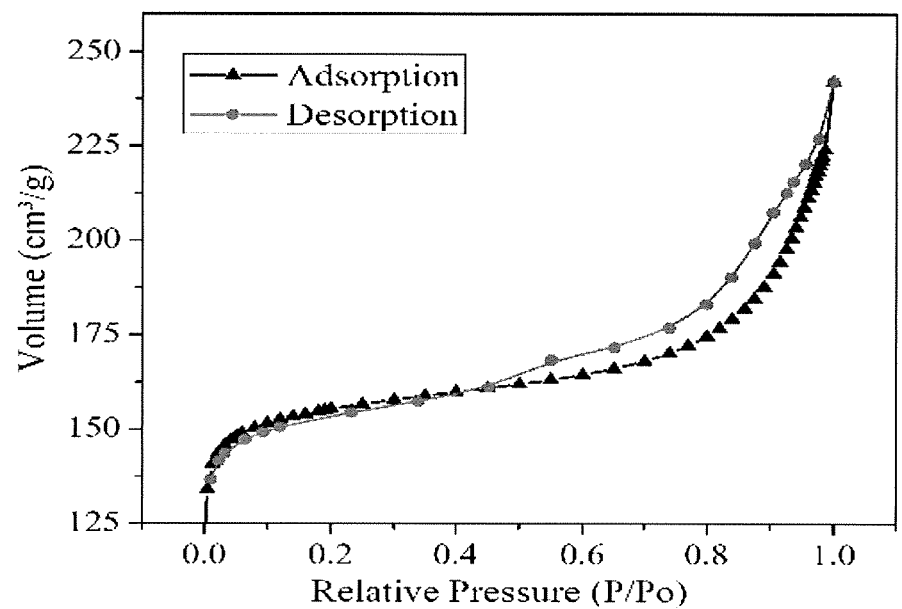
FIG. 4A-E. Nitrogen adsorption/desorption isotherms of the prepared bifunctional catalysts. A, Ru/HY; B, Ru—Fe/HY; C, Ru—Ni/HY; D, Ru—Cu/HY; E, Ru—Zn/HY.
Figure 4B:
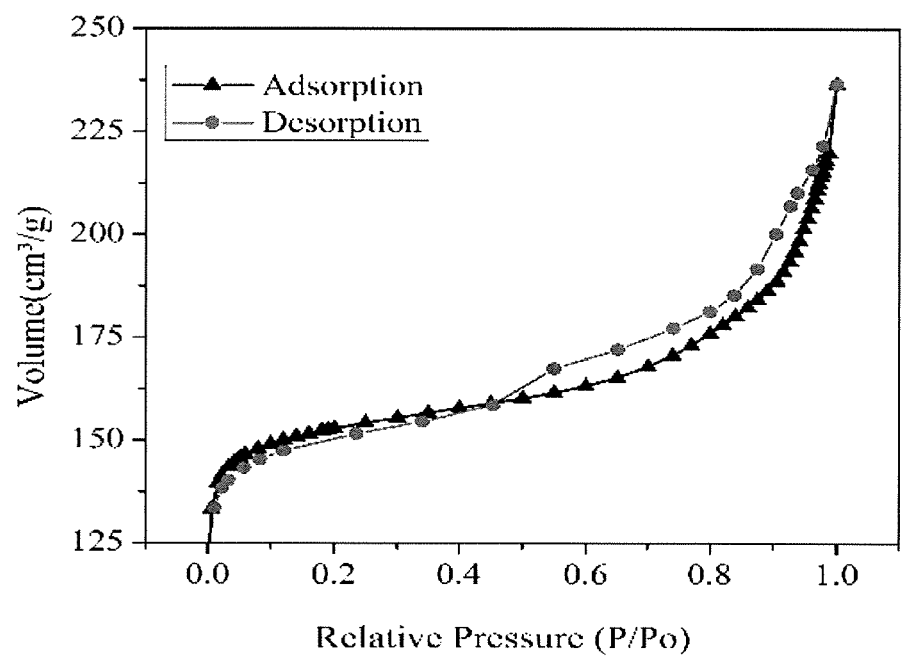
Figure 4C:
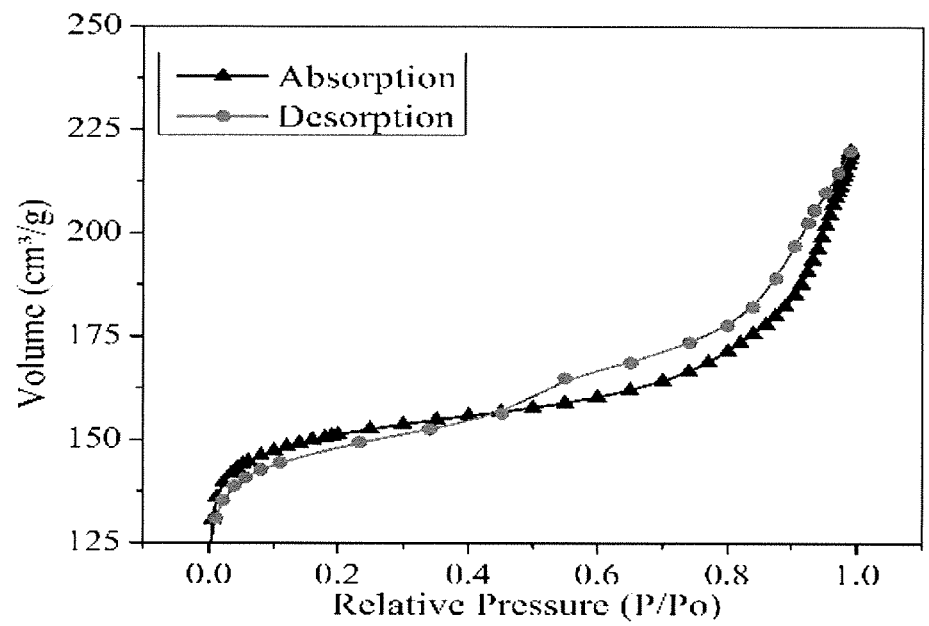
Figure 4D:
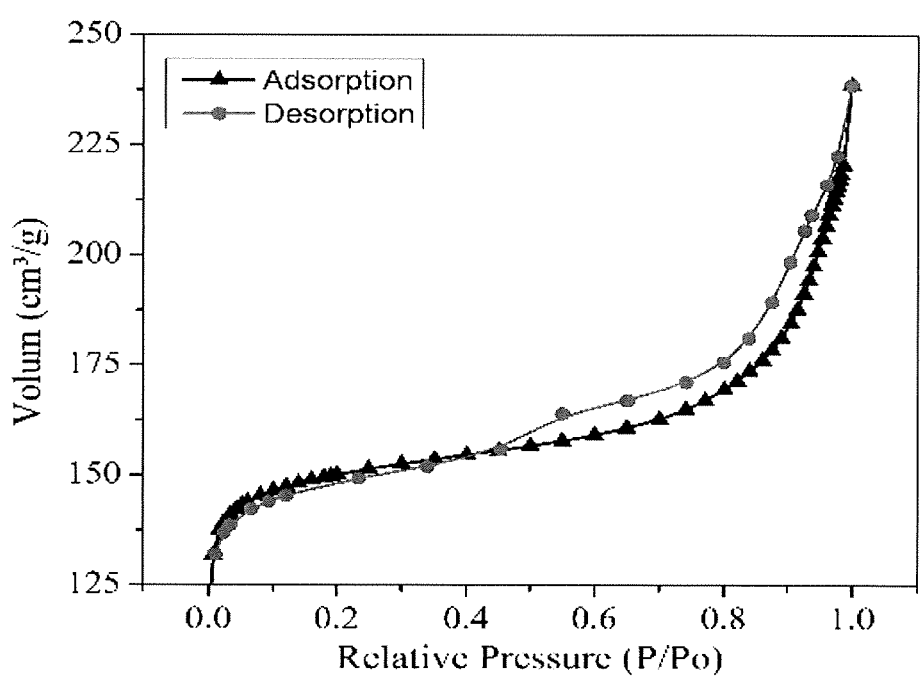
Figure 4E:
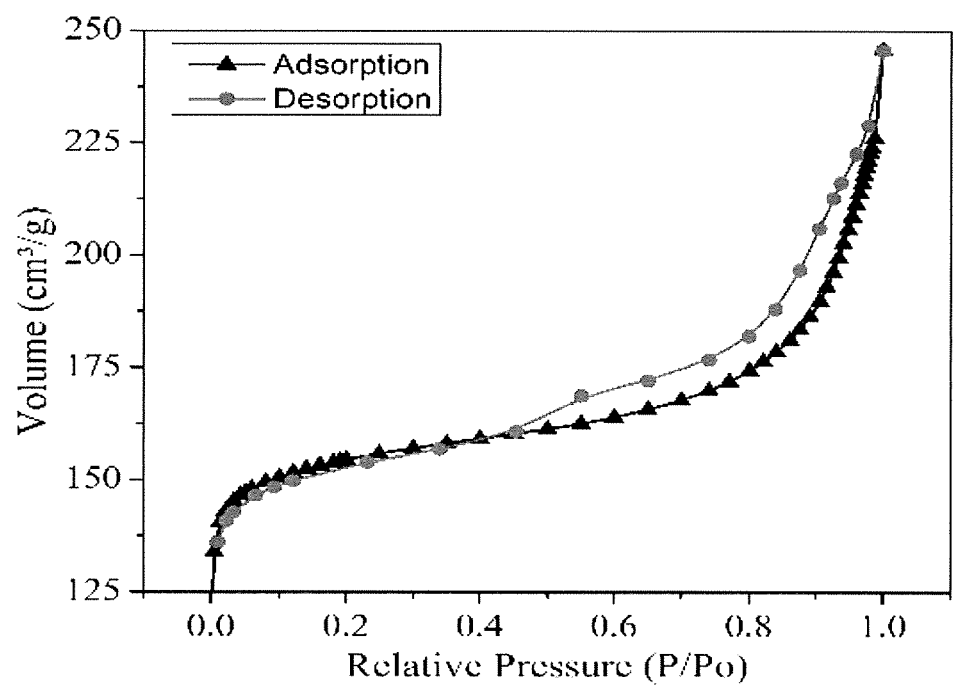

The detected products for all of the catalysts were similar and they were mainly cyclohexane derivatives with relatively high carbon numbers, as depicted in FIG. 3. A small fraction of oxy-compounds and ring-opening products were also detected. Products obtained were consistent with those produced via the combination catalysis of Ru/Al$_2$O$_3$ and H+—Y zeolite. The total yields of the detected hydrocarbon products were around 26 wt % to 32 wt %, which were higher than that found over the combination catalysis of Ru/Al$_2$O$_3$ and H+—Y zeolite (22 wt. %), indicating that the integration of metals with acidic zeolite can increase the catalytic selectivity of hydrocarbons from lignin HDO. The superior catalytic activity of Ru-M/H+—Y could be attributed to the so-called intimacy criterion (Zecevic, Nature 2015, 528 (7581), 245-248). In metal-acid bifunctional catalysts, the proximity of metal sites to acid sites is crucial for their catalytic capability. Large distances between metal and acid sites lead to low diffusivity of reaction intermediates, giving rise to gas and coke products via secondary reactions. Thus, for the two functional sites, the closer the better. In bifunctional catalysts of Ru-M/H+—Y, the distances between metal and acid sites are much smaller than that in the combination catalysts of Ru/Al$_2$O$_3$ with H+—Y zeolite.

Structural Characterization on Ru-based
Bifunctional Catalysts Supported on HY Zeolite

TABLE 4

Physical properties of HY zeolite and the synthesized catalysts

| Catalyst | BET surface area (m²/g) | Pore volume (cm³/g) | Average pore diameter (nm) |
|---|---|---|---|
| HY | 724 | 0.40 | 2.48 |
| Ru/HY | 608.52 | 0.37 | 2.46 |
| Ru—Fe/HY | 598.54 | 0.36 | 2.44 |
| Ru—Ni/HY | 591.13 | 0.34 | 2.29 |
| Ru—Cu/HY | 587.92 | 0.37 | 2.51 |
| Ru—Zn/HY | 604.53 | 0.38 | 2.46 |

In order to make clear why bimetallic catalysts of Ru-M/H$^+$—Y (M=Fe, Ni, Cu, Zn), especially Ru—Cu/H$^+$—Y, exhibited better catalytic performance than Ru/H$^+$—Y in HDO conversion of lignin models and real lignin, various characterizations were carried out to reveal the physical and chemical properties of these catalysts. Table 3 lists the surface area values, pore volumes and average pore diameters of H$^+$—Y zeolite and the synthesized bifunctional catalysts. The Brunauer-Emmett-Teller (BET) surface area of H$^+$—Y is 724 m²/g, while the BET surface area of all the five supported catalysts is about 600 m²/g. In spite of a decrease of BET surface area and closure of some of pores by active metals, all of the catalysts still had sufficiently high surface area to exhibit excellent catalytic properties. Typical nitrogen adsorption/desorption isotherms of the prepared catalysts are shown in FIG. 4. The isotherms showing similar type IV curves and porosities were obtained for all the synthesized catalysts, indicating that pore structures of these materials were mesoporous with narrow pore size distributions.

Results obtained from BET test and nitrogen adsorption/desorption suggest that all the prepared supported catalysts have relative high surface area values and keep the typical mesoporous structure of H$^+$—Y zeolites. The physical porosity of these catalysts are VERY similar, indicating that the differences in catalytic activity among the catalysts are not from these physical properties but from other influences.

TABLE 5

Acid properties of the prepared catalysts.

| Catalyst | Total mL NH$_3$/g cat | Total mol NH$_3$/g cat |
|---|---|---|
| Ru | 0.08870 | 3.96E-06 |
| Ru—Zn | 0.09895 | 4.42E-06 |
| Ru—Cu | 0.12318 | 5.50E-06 |
| Ru—Ni | 0.12269 | 5.48E-06 |
| Ru—Fe | 0.12998 | 5.80E-06 |

Figure 5:
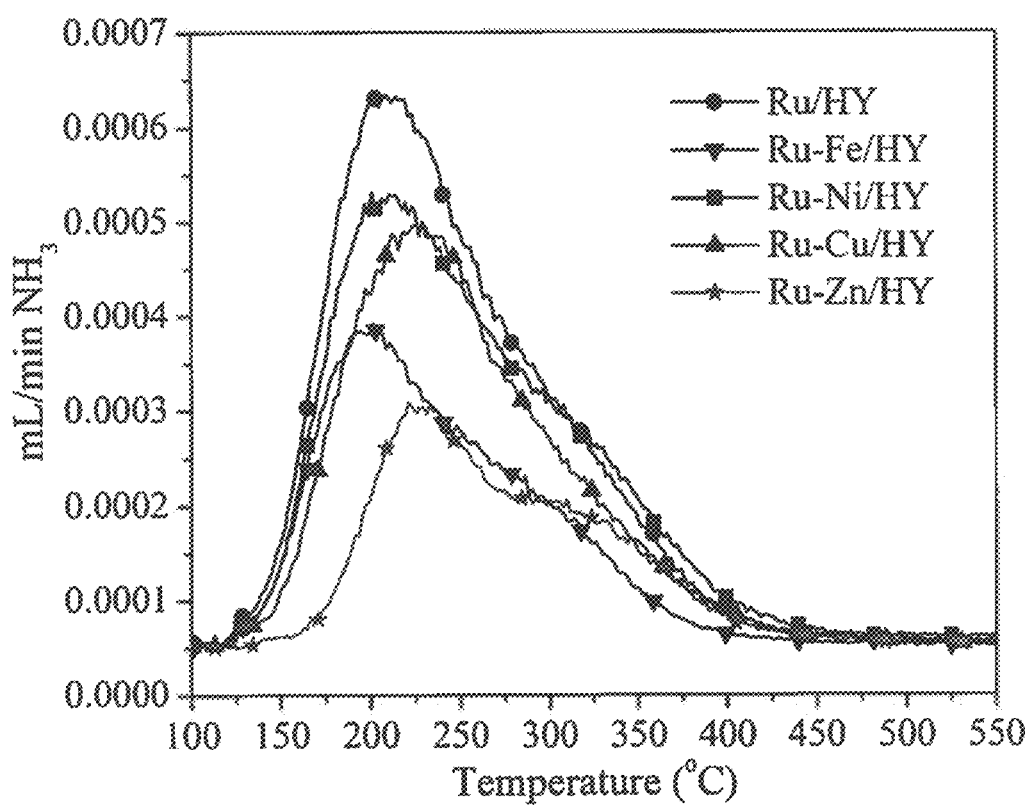
FIG. 5. NH$_3$-TPD curves of the synthesized bifunctional catalysts.

As indicated by other researchers, the conversion of lignin and the selectivity of products are strongly dependent on the acid properties of the catalyst that is used. Thus, NH$_3$-TPD measurements were carried out to determine the relationship between the activity of each catalyst and the number of acid sites. Table 4 lists the uptakes of NH$_3$ per one gram of catalysts, which reflects the number of acid sites in these catalysts. The acidity of the prepared bifunctional catalysts is mainly derived from the support of acidic H$^+$—Y zeolite. The impregnation of different metals in the support may result in different acid properties in the catalysts. It can be seen in Table 4 that there are indeed some slight differences in the number of acid sites in these catalysts which have different metals supported in them. If the catalysts are ranked by NH$_3$ uptake, two sets are obtained: Ru/H$^+$—Y and Ru—Zn/H$^+$—Y showed lower uptake compared to Ru—Cu/H$^+$—Y, Ru—Ni/H$^+$—Y, and Ru—Fe/H$^+$—Y, indicating that the total number of acid sites in the last three catalysts is slightly higher than that in Ru/H$^+$—Y and Ru—Zn/H$^+$—Y. The higher catalytic activity of Ru—Cu/H$^+$—Y in lignin HDO conversion may have some relationship with its higher number of acid sites. FIG. 5 shows the NH$_3$-TPD profiles of the prepared catalysts. The profile of NH$_3$ desorbed from the catalyst can be considered as the acid strength distribution on the catalysts. NH$_3$ adsorbed on strong acid sites could be desorbed at higher temperatures than that on weak acid sites. Something that is interesting is that, if the traces are deconvoluted, one observes that they all have essentially two peaks: one at about 200° C. and one at about 280° C. Later peaks indicate stronger acid sites on the catalyst. The ratio between the second to the first peak, is slightly larger in Ru—Zn/H$^+$Y, Ru—Cu/H$^+$—Y, and Ru—Ni/H$^+$—Y. Since Ru—Cu/H$^+$—Y, and Ru—Ni/H$^+$—Y are also the ones that show the higher NH$_3$ uptake, it could be that the Cu and Ni increase stronger acid sites preferentially.

Figure 6A:
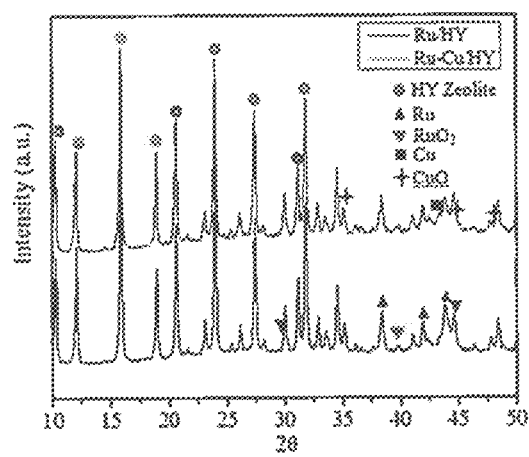
FIGS. 6A and B. XRD patterns for the synthesized bifunctional catalysts. A, Ru/HY and Ru—Cu/HY; B, Ru—Ni/HY and Ru—Zn/HY, FIG. 7A-D. Energy-dispersive X-ray spectroscopy for zeolite supported Ru-based bimetallic catalysts. A, Rule; B, RuNi; C, RuZn; D, RuCu.
Figure 6B:
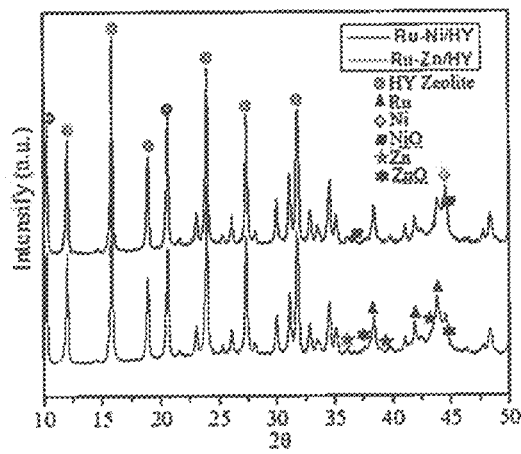
Figure 7A:
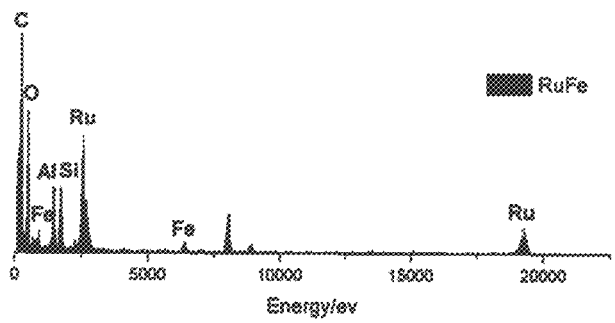
Figure 7B:
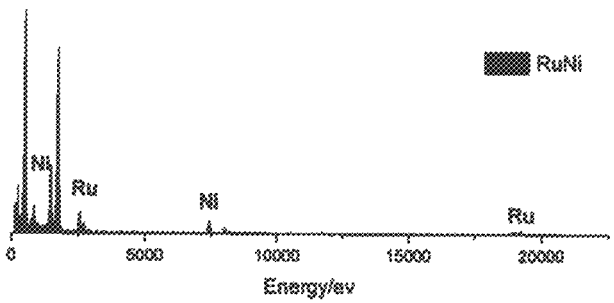
Figure 7C:
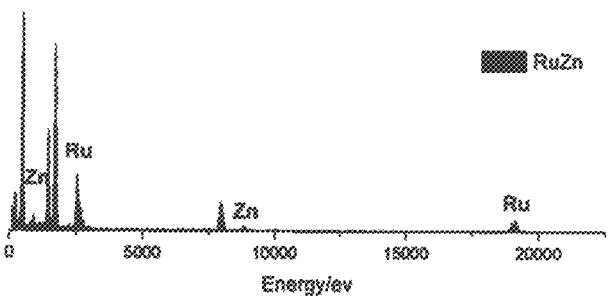
Figure 7D:
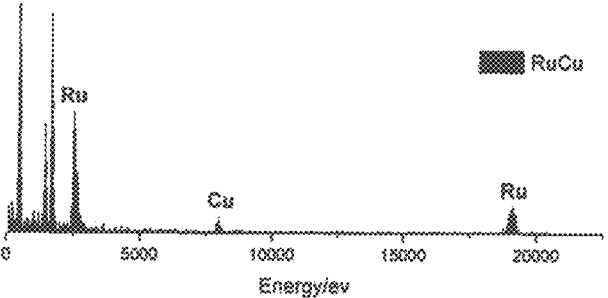
Figure 8:
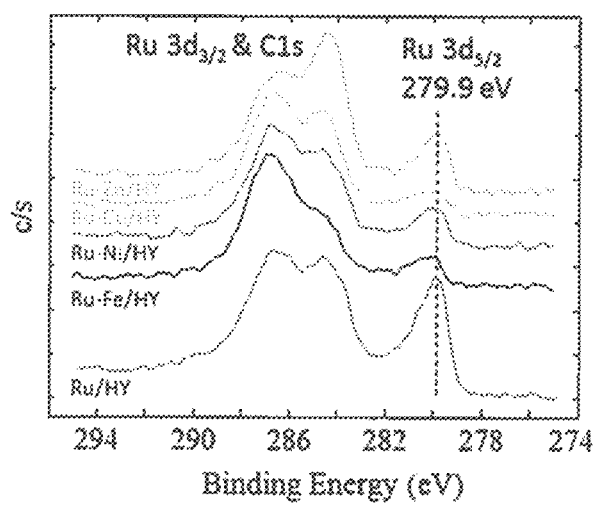
FIG. 8. High energy resolution X-ray photoemission spectra of the Ru 3d$_{5/2}$, Ru 3d$_{3/2}$ and C 1s regions.
Figure 9A:
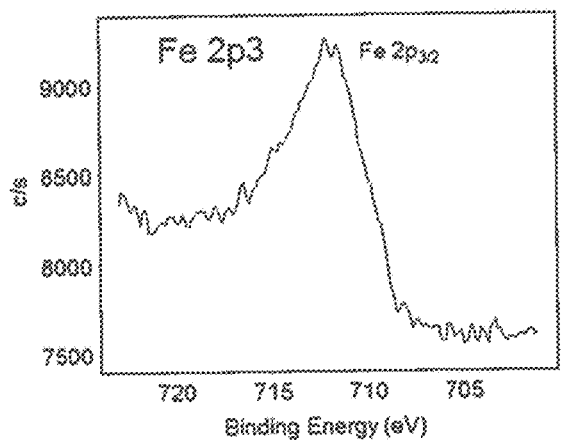
FIG. 9A-D. High energy resolution X-ray photoemission spectra of the Fe 2p$_{3/2}$, Ni 2p, Cu 2p, and Zn 2p$_{3/2}$ regions from catalysts A, Ru—Fe—HY, B, Ru—Ni/HY, C, Ru—Cu/HY and D, Ru—Zn/HY respectively.
Figure 9B:
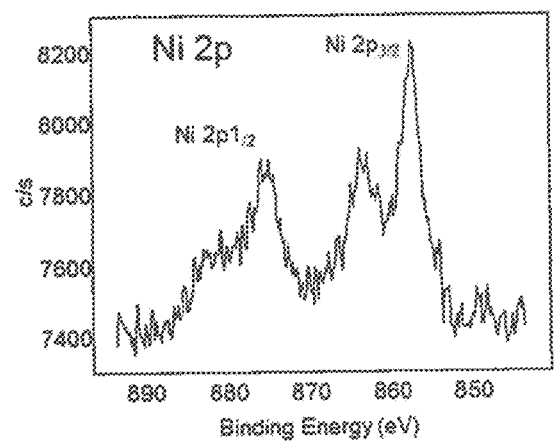
Figure 9C:
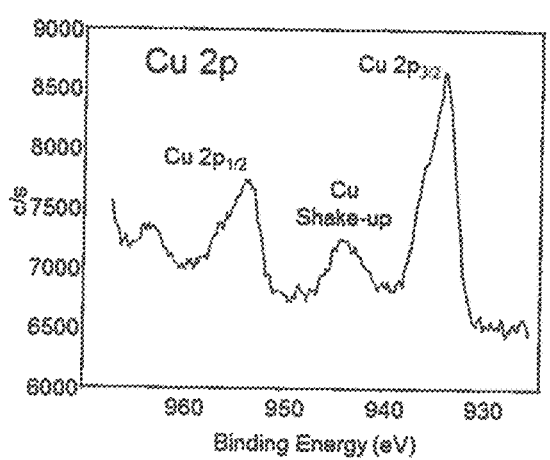
Figure 9D:
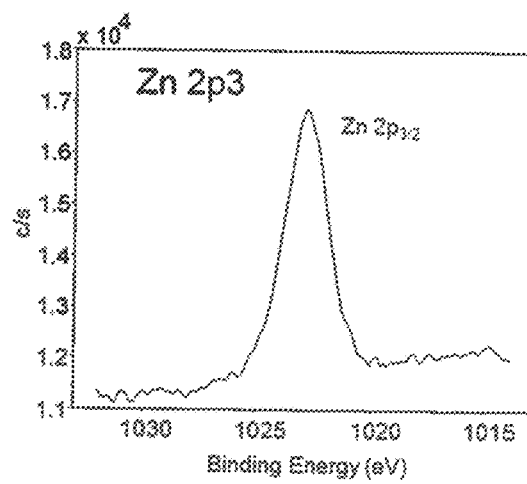

The phase and phase composition of the prepared catalysts were determined by XRD, as shown in FIG. 6. The XRD patterns of all the prepared bifunctional catalysts in the range of 2θ=10° to 2θ=33° are quite similar, and most of the peaks in this range could be assigned to the typical FAU structure of HY zeolite. The XRD pattern of the H$^+$—Y zeolite supported bifunctional catalysts at low 2θ angle completely matched with that of the parent of H$^+$—Y zeolite, indicating that the impregnation of metals in the support has no obvious effect on the parent zeolite structure. After impregnation, calcination, and reduction, metal species as well as their oxides might exist in the H$^+$—Y zeolite. The presence of formed reduced metals and metal oxides was not obvious from XRD patterns as compared with the signals of HY zeolite. This result is in accordance with previous investigations which revealed the diffraction signals of metal and metal oxide could not be easily observed upon incorporation into the zeolite structure when the metal loading was low or the metal oxides might be present as non-crystalline phase. Besides, good dispersion of metal species and limited segregation of the relative oxide particles could also prevent the metal and metal oxides species from being observed with XRD.

Though the XRD signals of metal and metal oxides are not as strong as that of H$^+$—Y, they are sufficient to show the existence of different metals and metal oxides supported on the synthesized catalysts, as shown in FIG. 6 (2θ=33° to 2θ=50°). Moreover, the XRD reflections indicate indirectly a synergistic effect of a second metal in bimetallic Ru-M (M=Fe, Ni, Cu, Zn) catalysts. The addition of a second metal definitely changes the morphology and the crystalline nature of the Ru present in the H$^+$—Y zeolite, as evidenced from FIG. 6. Also, the relative intensity of the peaks such as 2θ=43.8° was reduced when compared to the pure Ru-supported catalyst, indicating the well-dispersed nature of the bimetallic catalysts. These observations indicate that the addition of a second metal to Ru enables Ru to form much smaller particles that are mixed with the second metal after the hydrogen reduction.

As indicated by the XRD, a part of the 3d transition metals existed in the bimetallic catalysts were not totally reduced, so that some metal oxides remained in the acidic support of H$^+$—Y zeolite. Both the acidic HY zeolite and oxides can catalyze reactions that eliminate some of the oxygenated functionalities while building up the C—C chain. For instance, ketonization, oligomerization, and transalkylation of methoxy groups, catalyzed by acids and oxides, maximize the fraction of carbon that is ultimately retained in the liquid product. Moreover, Montassier and co-authors suggested that Cu metal has a high adsorption capacity for polar fractions (including hydroxyl group and ether bonds) due to its electrophilicity, and this adsorption leads to a weakening of the O—H and C—O bond. This propensity for adsorbing polar fractions might be enhanced when Cu associated with noble metals or metals with a lower d orbital electron occupancy, which can accept electrons from Cu leading to an increase in the Cu atom's electrophilicity, and this phenomenon can possibly account for the higher HDO reactivity of Ru—Cu/H$^+$—Y catalyst.

The morphology and microstructure of the synthesized bifunctional catalysts were investigated by STEM (not shown). The average metal particle size for the monometallic catalyst of Ru/HY is about 10~15 nm, which is larger than that supported on other materials reported in previous studies. Ru metal particles tend to form some compact clusters with diameter around 50 nm. Interestingly, bimetallic nanoparticles have a smaller average size and a narrower size distribution when compared with monometallic Ru nanoparticles. The bimetallic particle sizes are about 3~5 nm, 3~6 nm, 6~8 nm, and 8~10 nm for Ru—Cu/H$^+$—Y, Ru—Ni/H$^+$—Y, Ru—Fe/H$^+$—Y, and Ru—Zn/H$^+$—Y catalysts, respectively. Moreover, the morphology of these bimetallic clusters is quite different from that of ruthenium monometallic particles. For example, the bimetallic Ru—Cu clusters are rather loose. The different size and morphology of monometallic Ru particles compared to bimetallic clusters indicates the existence of a strong synergetic effect between Ru and the transition metals. It is well known that the catalytic activity of a supported metal catalyst is highly dependent on the metal particle/cluster size and metal particle/cluster morphology. Metal particles/clusters with small size and/or a non-compact structure have large fractions of the atoms exposed to reactants, resulting in high/unique catalytic activities. The Ru—Cu bimetallic nanoparticles on H$^+$—Y are well-dispersed without any obvious aggregation.

All of the aforementioned factors (e.g., large surface area/small particle size, strong synergetic effect between Ru and a second metal, and bimetallic nanoparticles with high dispersion) could contribute to the observed improvements in the activity of the catalysts for the hydrodeoxygenation conversion of lignin and its model compounds.

Conclusion

Bifunctional catalyst Ru-M/H$^+$—Y (M=Fe, Ni, Cu, Zn) was synthesized and evaluated on HDO conversion of softwood lignin as well as several lignin model compounds, including guaiacol, diphenyl ether, (benzyloxy)benzene and benzofuran. Results obtained from guaiacol HDO reaction indicated that all the bimetallic catalysts, especially Ru—Cu/H$^+$—Y, exhibited better HDO catalytic activities (regarding to guaiacol conversion and hydrocarbon yield) as compared with Ru/H$^+$—Y. This result is due to that the combination of a 3d transition metal (Fe, Ni, Cu, Zn) with Ru can mitigate the hydrogenolysis activity of Ru and prevent the hydrocarbon products from overhydrogenolysis to form low molecular gas products. Isomerization and dimerization reactions were observed over the prepared catalysts. Results from conversion of other lignin model compounds and softwood lignin also revealed the high HDO catalytic activity of the prepared bimetallic catalyst. The yield of hydrocarbon products over the synthesized bifunctional catalysts were higher than that over the combination catalysis of Ru/Al$_2$O$_3$ and H$^+$—Y zeolite, which could be probably ascribed to the intimacy criterion. These catalysts were characterized by BET, NH$_3$-TPD, XRD, and STEM to study the relationship of their structure with their catalytic activity. Results from the BET test indicate that all the prepared catalysts have high enough surface area values (about 600 m$^2$/g) for catalytic purposes, although an obvious decrease in surface area was noticed as compared to the unsupported H$^+$—Y zeolite. Ru—Cu/H$^+$—Y has both higher acid volume and larger ratio of stronger acid sites as compared to other prepared bifunctional catalysts. Results from XRD test indicated the impregnation of metals in the H$^+$—Y support has little effect on the parent zeolite structure. Moreover, both XRD and STEM results suggested that the addition of a second metal to Ru would have enabled Ru to form particles with much smaller size. The morphology of the bimetallic clusters is also found to be quite different (smaller average size and narrow size distribution) from that of monometallic particles as indicated by STEM.

While the invention has been described in terms of its preferred aspects, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of producing at least one hydrocarbon from lignan, comprising
exposing a reaction mixture comprising lignin to a bimetallic catalyst having of chemical formula Ru-M/XY, where M is a metal, Y is a Y zeolite and X is a cation associated with the Y zeolite, wherein the step of exposing is performed under conditions suitable for hydrodeoxygenation of lignin in the reaction mixture; and
recovering at least one cyclic alkane from the reaction mixture after hydrodeoxygenation of the lignin.

2. The method of claim 1 wherein M is selected from the group consisting of Fe, Ni, Cu, and Zn.

3. The method of claim 1 wherein the cation is selected from the group consisting of H+, Na$^+$, K$^+$ and NH$^{4+}$.

4. The method of claim 1 wherein the at least one cyclic alkane is a cyclohexane derivative.

5. The method of claim 4 wherein the cyclohexane derivative is selected from the group consisting of methylcyclohexane, ethylcyclohexane, 1,1'-bi(cyclohexane), dicyclohexylmethane and 1,2-dicyclohexylethane.

6. The method of claim 1 wherein the at least one cyclic alkane is a fuel or a fuel additive.

7. The method of claim 6 wherein the fuel or the fuel additive is selected from the group consisting of a paraffin, an indan, a tetralin, a cycloolefin, a cyclohexanone and a cyclohexanol derivative.

8. The method of claim 7, wherein the fuel or the fuel additive is a paraffin and the paraffin is a monocycloparaffin, a dicycloparaffin or a tricycloparaffin.

* * * * *